United States Patent
Bektesevic et al.

(10) Patent No.: US 8,927,791 B2
(45) Date of Patent: Jan. 6, 2015

(54) METHOD FOR PRODUCING TETRAFLUOROPROPENES

(75) Inventors: Selma Bektesevic, Morristown, NJ (US);
Hsueh S. Tung, Morristown, NJ (US);
Haiyou Wang, Morristown, NJ (US);
Daniel C. Merkel, Morristown, NJ (US);
Robert C. Johnson, Morristown, NJ (US)

(73) Assignee: Honeywell International Inc., Morristown, NJ (US)

( * ) Notice: Subject to any disclaimer, the term of this patent is extended or adjusted under 35 U.S.C. 154(b) by 305 days.

(21) Appl. No.: 13/073,023

(22) Filed: Mar. 28, 2011

(65) Prior Publication Data
US 2011/0270000 A1 Nov. 3, 2011

Related U.S. Application Data

(60) Provisional application No. 61/329,327, filed on Apr. 29, 2010.

(51) Int. Cl.
| | | |
|---|---|---|
| *C07C 17/00* | (2006.01) | |
| *C07C 17/25* | (2006.01) | |
| *C07C 19/08* | (2006.01) | |
| *C07C 21/18* | (2006.01) | |
| *C07C 17/21* | (2006.01) | |
| *C07C 17/087* | (2006.01) | |

(52) U.S. Cl.
CPC ............... *C07C 17/21* (2013.01); *C07C 17/087* (2013.01); *C07C 17/25* (2013.01)
USPC .......................................... 570/156

(58) Field of Classification Search
None
See application file for complete search history.

(56) References Cited

U.S. PATENT DOCUMENTS

| | | |
|---|---|---|
| 6,124,510 A | 9/2000 | Elsheikh et al. |
| 6,548,719 B1 | 4/2003 | Nair et al. |
| 2003/0060670 A1 | 3/2003 | Nair et al. |
| 2005/0090698 A1 | 4/2005 | Merkel et al. |
| 2007/0100175 A1 | 5/2007 | Miller et al. |
| 2007/0197842 A1* | 8/2007 | Mukhopadhyay et al. ... 570/155 |
| 2009/0030247 A1* | 1/2009 | Johnson et al. .............. 570/155 |
| 2009/0043136 A1 | 2/2009 | Wang et al. |
| 2009/0099396 A1 | 4/2009 | Mukhopadhyay et al. |
| 2009/0182179 A1 | 7/2009 | Merkel et al. |
| 2012/0184785 A1* | 7/2012 | Cottrell et al. ............... 570/153 |

FOREIGN PATENT DOCUMENTS

| WO | 2008030440 | 3/2008 |
|---|---|---|
| WO | 2008075017 A2 | 6/2008 |

OTHER PUBLICATIONS

European Supplemental Search Report issued in 11777886.0 dated Aug. 9, 2013.

* cited by examiner

*Primary Examiner* — Clinton Brooks
(74) *Attorney, Agent, or Firm* — Bruce Bradford

(57) ABSTRACT

The current invention relates to a process for making a tetrafluoropropene using a tetrafluorochloropropane and/or a pentafluoropropane as starting or intermediate reagents. More specifically, though not exclusively, the present invention relates to a novel method for preparing a tetrafluoropropene by dehydrohalogenating a starting or intermediate tetrafluorochloropropane and/or pentafluoropropane material in the presence of a caustic solution at a temperature range greater than 40° C. and less than or equal to 80° C.

12 Claims, No Drawings

METHOD FOR PRODUCING TETRAFLUOROPROPENES

CROSS-REFERENCE TO RELATED APPLICATIONS

This application is related to and claims the priority benefit of U.S. provisional application No. 61/329,327 filed Apr. 29, 2010, the contents of which are incorporated herein by reference.

FIELD OF THE INVENTION

This invention relates to a novel method for preparing fluorinated organic compounds, more particularly to a method for preparing fluorinated olefins, and even more particularly to a method for producing a tetrafluoropropene.

BACKGROUND OF THE INVENTION

Hydrofluoroolefins (HFOs), such as tetrafluoropropenes (including 2,3,3,3-tetrafluoroprop-1-ene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. In addition, HFO-1234yf is a low global warming compound with low toxicity and hence can meet increasingly stringent requirements for refrigerants in mobile air conditioning.

Two known precursors used to prepare HFO-1234yf include 1,1,1,2-tetrafluo-2-chlororopropane (HCFC-244bb) and 1,1,1,2,2-pentafluoropropane (HFC-245cb). Indeed, numerous gas phase reactions are known for the production of HFO-1234yf by HCFC-244bb dehydrochlorination, and HFC-245cb dehydrofluorination, respectively. U.S. Pub. No. US2007/0197842, for example, teaches the synthesis of HFO-1234yf through gas phase HCFC-244bb dehydrochlorination in the presence of a carbon- and/or metal-based catalyst (e.g. nickel or palladium based catalysts). U.S. Pub. No. US2009/0043136 teaches the preparation of HFO-1234yf through gas phase HCFC-244bb dehydrochlorination in the presence of a catalyst selected from the group consisting of (i) one or more metal halides, (ii) one or more halogenated metal oxides, (iii) one or more zero-valent metals/metal alloys, or (iv) a combination of two or more of the foregoing. U.S. Pub. No. US2007/0100175 teaches the production of HFO-1234yf through gas phase HFC-245cb dehydrofluorination in the presence of a catalyst selected from the following: aluminum fluoride; fluorided alumina; metals on aluminum fluoride; metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid-washed carbon, activated carbon, three dimensional matrix carbonaceous materials; and metal compounds supported on carbon. Applicants, however, have recognized that these gas phase dehydrohalogenation reactions are operated at a high temperature, typically above 400° C., to obtain meaningful yield. Because higher temperature can increase costs associated with production, there is a need in the art for a new and convenient low temperature process of preparing HFO-1234yf from HCFC-244bb and/or HFC-245cb.

While not specifically relating to the production of HFO-1234yf, U.S. Pat. No. 6,548,719 does disclose a low temperature process for producing fluoroolefins by dehydrohalogenating a halofluorocarbon with an alkali metal hydroxide in the presence of a phase transfer catalyst. The reaction is conducted at a temperature range of $-5°$ C. to $40°$ C. with an optimal temperature being about $25°$ C. While numerous starting reagents are exemplified for the production of HFO-1234ze, HFO-1225zc, and $CF_3CBr=CF_2$, U.S. Pat. No. 6,548,719 does not expressly provide, however, a method for manufacturing HFO-1234yf, let alone a dehydrohalogenation method using HCFC-244bb and/or HFC-245cb as starting reagents. Furthermore, the exemplified reaction temperature ($-5°$ C. to $40°$ C.) is too low to achieve meaningful activity with 244bb/245cb dehydrohalogenation because the halogen to be eliminated in 244bb/245cb is attached to the middle carbon, which is more difficult to be removed. Accordingly, there is a continuing need for a new low temperature process for preparing HFO-1234yf from HCFC-244bb and/or HFC-245cb.

The present invention and the embodiments presented herein address at least this need.

SUMMARY OF THE INVENTION

In one embodiment, the present invention relates to a process for making a tetrafluoropropene by dehydrohalogenating a tetrafluorochloropropane or a pentafluoropropane in the presence of a caustic agent at a temperature range greater than $40°$ C. and less or including $80°$ C. In certain aspects of the invention, the tetrafluorochloropropane is 1,1,1,2-tetrafluoro-2-chloropropane, the pentafluoropropane is 1,1,1,2,2-pentafluoropropane, and the tetrafluoropropene is 2,3,3,3-tetrafluoropropene. The caustic agent may include, but is not limited to, an alkali metal hydroxide, an alkali metal oxide, an alkaline earth metal hydroxide, an alkaline earth metal oxide and combinations thereof. Such caustic agents may include KOH, NaOH, LiOH, $Mg(OH)_2$, $Ca(OH)_2$, CaO and combinations thereof. In certain embodiments, the caustic agent is potassium hydroxide (KOH), which may be provided as an aqueous solution having about 5% to about 95% by weight of KOH.

Reaction pressures of the dehydrohalogenation process may range from atmospheric pressure to super-atmospheric pressure or sub-atmospheric.

The dehydrohalogenation process also may occur in the presence of a phase transfer catalyst, as defined herein. Such phase transfer catalysts may include, but are not limited to, crown ethers, onium salts, cryptates, polyalkylene glycols, derivatives thereof, and combinations thereof. In one embodiment, the phase transfer catalyst is Aliquat 336.

In another non-limiting embodiment, the present invention relates to a process for preparing a tetrafluoropropene by (a) contacting 2-chloro-3,3,3-trifluoropropene (HCFO-1233xf) with hydrogen fluoride in the presence of a fluorination catalyst to produce an intermediate compound selected from the group consisting of a tetrafluorochloropropane, a pentafluoropropane, and combinations thereof; (b) optionally, recovering the intermediate; and (c) contacting said intermediate with a caustic agent within a temperature range greater than $40°$ C. and less than or equal to $80°$ C. In certain aspects of the present invention, the tetrafluorochloropropane is 1,1,1,2-tetrafluoro-2-chloropropane and/or the pentafluoropropane is 1,1,1,2,2-pentafluoropropane. The caustic agent of the last step may include, but is not limited to, an alkali metal hydroxide, an alkali metal oxide, an alkaline earth metal hydroxide, an alkaline earth metal oxide and combinations thereof. Such caustic agents may include KOH, NaOH, LiOH, $Mg(OH)_2$, $Ca(OH)_2$, CaO and combinations thereof. In certain embodiments, the caustic agent is potassium hydroxide (KOH), which may be provided as an aqueous solution having of about 5% to about 95% by weight of KOH.

Reaction pressures of the dehydrohalogenation process may range from atmospheric pressure to super-atmospheric pressure or sub-atmospheric.

The dehydrohalogenation process may occur in the presence of a phase transfer catalyst, as defined herein. Such phase transfer catalysts may include, but are not limited to, crown ethers, onium salts, cryptates, polyalkylene glycols, derivatives thereof, and combinations thereof. In one embodiment, the phase transfer catalyst is Aliquat 336.

In an even further embodiment, the present invention relates to a process for making 2,3,3,3-tetrafluoropropene by dehydrohalogenating 1,1,1,2-tetrafluoro-2-chloropropane and 1,1,1,2,2-pentafluoropropane in the presence of a caustic agent at a temperature range greater than 40° C. and less than or equal to 80° C.

The dehydrohalogenation reaction steps of the present invention are particularly advantageous because of the disclosed temperature range of above 40° C. and below or about 80° C. This temperature range is shown herein to surprisingly increase both the conversion yield and reaction rate. Additional embodiments and advantages of the present invention will be readily apparent to one of ordinary skill in the art based on the disclosure and teachings herein.

DETAILED DESCRIPTION OF THE INVENTION

The present invention relates to a process for making a tetrafluoropropene, including 2,3,3,3-tetrafluoropropene (HFO-1234yf), using a tetrafluorochloropropane and/or a pentafluoropropane as starting or intermediate reagents. In certain aspects, the definition of tetrafluorochloropropane refers to a three carbon alkyl chain having four fluorine atoms and one chlorine atom. In certain embodiments, the tetrafluorochloropropane is 1,1,1,2-tetrafluoro-2-chloropropane (HCFC-244bb). In further aspects, the definition of pentafluoropropane refers to a three carbon alkyl chain having five fluorine atoms. In certain embodiments, the pentafluoropropane is 1,1,1,2,2-pentafluoropropane (HFC-245cb). While in numerous embodiments discussed herein the tetrafluorochloropropane is defined as HCFC-244bb and/or the pentafluoropropane is defined as HFC-245cb, one of skill in the art will appreciate that such embodiments are not limiting to the invention and that HCFC-244bb or HFC-245cb may be substituted with any tetrafluorochloropropane or pentafluoropropane, respectively.

In certain embodiments, the present invention relates to a novel method for preparing HFO-1234yf comprising the steps of (a) contacting a starting material of 2-chloro-3,3,3-trifluoropropene (HCFO-1233xf) with hydrogen fluoride in the presence of a fluorination catalyst to produce an intermediate comprising a tetrafluorochloropropane and/or a pentafluoropropane, (b) optionally, recovering said intermediate, and (c) contacting said intermediate with a caustic solution under conditions effective to produce a reaction product comprising HFO-1234yf.

The initial step of hydrofluorinating HCFO-1233xf, may be performed using reaction conditions known in the art, such as that disclosed in U.S. application Ser. No. 12/338,466, the contents of which are incorporated herein by reference. To this end, in one embodiment catalysts are employed to enhance the single-pass conversion of HCFO-1233xf to a tetrafluorochloropropane (e.g. HCFC-244bb) via HF addition across the double bond of HCFO-1233xf. Some pentafluoropropane (e.g. HFC-245cb) also may be generated as useful by-product. Catalysts for performing this step may include, but are not limited to, $SbCl_3$, $SbCl_5$, $SbF_5$, $TiCl_4$, $SnCl_4$, $Cr_2O_3$, and fluorinated $Cr_2O_3$. As discussed below, the hydrofluorination process may be carried out in a vapor phase or a liquid phase.

In vapor-phase hydrofluorination, HF (hydrogen fluoride gas) is fed continuously through the catalyst bed. After a short time with only the HF feed stream, HCFO-1233xf is fed continuously through the catalyst bed at a ratio of about 1:1 to about 1:30 and, in certain embodiments, from about 1:2 to about 1:15 (HCFO-1233xf/HF mole ratio). The reaction between HF and HCFO-1233xf is carried out at a temperature from about 30° C. to about 400° C. (in further embodiments from about 100° C. to about 300° C.) and at a pressure of about 5 psia to about 200 psia (pounds per square inch absolute) (in further embodiments from about 30 psia to about 175 psia). The catalyst may be supported on a substrate, such as on activated carbon, or may be unsupported or free-standing. In addition to activated carbon, useful catalyst supports include: alumina, fluorinated alumina, aluminum fluoride, alkaline earth metal oxides, fluorinated alkaline earth metals, zinc oxide, zinc fluoride, tin oxide, and tin fluoride. The catalyst may (or may not) have to be activated with anhydrous hydrogen fluoride HF (hydrogen fluoride gas) before use depending on the state of the catalyst.

In liquid phase hydrofluorination, the catalyst is charged in a liquid form to a reactor and optionally activated with HF. The activated catalyst is then heated to the desired reaction temperature of about 30° C. to about 200° C. (in further embodiments from about 50° C. to about 120° C.) and the pressure is kept between about 15 psia to about 200 psia (in further embodiments from about 50 psia to about 175 psia). After a short time with only HF feed, a HCFO-1233xf feed stream is fed continuously through the catalyst at a ratio of about 1:1 to about 1:30 and in further embodiments about 1:2 to about 1:15 (HCFO-1233xf/HF mole ratio). If necessary, the catalyst can be kept activated by the continuous or batch addition of $Cl_2$ or a similar oxidizing agent.

In certain embodiments, the hydrofluorination reaction is carried out to attain a conversion of about 70% or more, in further embodiments about 90% or more, and in even further embodiments about 93% or more. Conversion is calculated by the number of moles of reactant (HCFO-1233xf) consumed divided by number of moles of reactant (HCFO-1233xf fed to the reactor multiplied by 100. The selectivity for the tetrafluorochloropropane (e.g. HCFC-244bb) attained is about 60% or in further embodiments about 80% or more. Selectivity is calculated by number of moles of product formed divided by number of moles of reactant consumed.

Hydrofluorination may be carried out in a corrosion-resistant reaction vessel. Examples of corrosion-resistant materials are Hastelloy, Nickel, Incoloy, Inconel, Monel and fluoropolymer linings. The vessel may have a fixed catalyst bed, or contain liquid catalyst. If desired, inert gases such as nitrogen or argon may be employed in the reactor during operation.

The foregoing hydrofluorination steps are not necessarily limiting to the present invention, however, and may also include derivative or alternative methodologies that are otherwise known in the art.

Once the tetrafluorochloropropane and/or pentafluoropropane is produced, it may be optionally separated from the product stream before being fed into dehydrohalogenation reactor. Such separation methods are non-limiting to the present invention, however, and may be provided using any means known in the art, such as extraction, distillation, or the like. In one non-limiting embodiment, separation is achieved based upon one or more properties of these compounds, e.g. melting point, freezing point, boiling point, or the like. Alternatively, these components may be separated based upon known azeotrope or azeotrope-like compositions formed with one or more reagents or by-products in the reaction. In even further alternatives, the tetrafluorochloropropane and/or pentafluoropropane may be extracted using other methods known to one of ordinary skill in the art.

The final step of the present invention includes the dehydrohalogenation of the tetrafluorochloropropane and/or pentafluoropropane to form HFO-1234yf. In certain embodiments, the tetrafluorochloropropane and/or pentafluoropropane is contacted with a caustic dehydrohalogenating agent to form the HFO-1234yf. As used herein, a "caustic" material or agent refers to a light metal hydroxide or oxide compound. Such caustic materials may include, but are not limited to, alkali metal hydroxides and oxides and alkali earth metal hydroxides and oxides. Exemplified alkali metal hydroxides include, but are not limited to, potassium hydroxide (KOH), sodium hydroxide (NaOH), lithium hydroxide (LiOH), and combinations thereof. Alkali earth metal hydroxides and oxides include, but are not limited to, magnesium hydroxides ($Mg(OH)_2$), calcium hydroxides ($Ca(OH)_2$), calcium oxides (CaO) and combinations thereof. Generally speaking, on a mole basis, excess amounts of caustic materials relative to the amount of organic is used to help increase the conversion.

In one non-limiting embodiment, the caustic material is potassium hydroxide (KOH). KOH may be provided as an aqueous solution comprising from about 5% to about 62%, in further embodiments from about 10% to about 55%, and in even further embodiments from about 30% to about 50% by weight of the caustic material. In carrying out the process, the molar ratio of KOH to the tetrafluorochloropropane and/or pentafluoropropane is from about 1 to about 15; in further embodiments from about 1 to about 10; and in even further embodiments from about 1 to about 5. Again, such molar amounts are not necessary limiting to the invention and any amount, including excess KOH, may be provided to facilitate conversion.

Embodiments using KOH as the caustic material and HCFC-244bb and/or HFC-245cb as the starting material may be described, by way of illustration but not necessarily by way of limitation, by the following reaction equations:

(1)

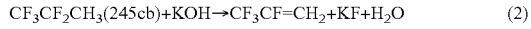
(2)

Such dehydrohalogenation is carried out under conditions effective to provide a HCFC-244bb and/or HFC-245cb conversion of at least about 40%, in further embodiments at least about 55%, and in even further embodiments at least about 70%. In certain embodiments the conversion is at least about 90%, and in further embodiments about 100%. In certain further embodiments, the HCFC-244bb and/or HFC-245cb is converted under conditions effective to provide a selectivity to HFO-1234yf of at least about 85%, in further embodiments at least about 90%, and in even further embodiments at least about 95%, and in even further embodiments about 100%. This reaction may be performed as a liquid phase reaction, although in certain embodiments it may comprise a gas phase, solid phase or a combination of gas, liquid, or solid phase reactions. It is contemplated that the reaction can be carried out batch wise, continuous, or a combination of these.

Pressure conditions for the dehydrohalogenation reaction are considered non-limiting to the invention. To this end, reaction pressure may vary, depending on particular or desired processing parameters of each application and may range from atmospheric pressure to super-atmospheric pressure or sub-atmospheric pressure.

In one embodiment, a temperature range of above 40° C. and below or including 80° C. is desirable to control the dehydrohalogenation conversion yield and rate. In further embodiments, the dehydrohalogenation steps occur at approximately 55° C. This temperature range is found to be surprisingly advantageous for the conversion reaction. As noted previously, lower reaction temperatures (e.g. those below 40° C.) are too low to achieve meaningful conversion because the halogen to be eliminated in 244bb/245cb is attached to the middle carbon. At such lower temperatures, the internal halogen is more difficult to be removed than those attached to the end carbon. A reaction temperature greater than 40 and less than or equal to 80° C. has been surprisingly found to increase conversion and the rate of reaction, thus, leading to more efficient yields and shortened reaction times. Accordingly, this temperature range is advantageous over and above known reaction conditions.

Based on the foregoing, prior to proceeding with the dehydrohalogenation reaction, the caustic solution and/or reactants may be brought within the desired temperature range. This range may include from about 20° C. to about 100° C., in further embodiments from about 30° C. to about 90° C., and in even further embodiments from about 40° C. to about 80° C. As discussed above, the latter temperature range is most desirable as it facilitates the surprising increase in product yield and reaction rate.

The dehydrohalogenation reaction also can be carried out in the absence or presence of phase transfer agent. A phase transfer catalyst is a substance that facilitates the transfer of ionic compounds (e.g. reactants or components) into an organic phase form (e.g. a water phase). For example, an aqueous or inorganic phase may be present as a consequence of the caustic material and an organic phase present as a result of the fluorocarbon. A phase transfer catalyst facilitates the reaction of these two incompatible components. Phase transfer catalysts can be ionic or neutral and may include, but not limited to, crown ethers, onium salts, cryptates and polyalkylene glycols or derivatives thereof.

Crown ethers (e.g. cyclic molecules in which ether groups are connected by dimethylene linkages) may include, but are not limited to, 18-crown-6, 15-crown-5, 12-crown-4. Derivatives of the above crown ethers are also useful, e.g., dibenzo-18-crown-6, dicyclohexano-18-crown-6, and dibenzo-24-crown-8 as well as 12-crown-4. Other polyethers particularly useful for alkali metal compounds, and especially for lithium, are described in U.S. Pat. No. 4,560,759 which is incorporated herein by reference. Other compounds analogous to the crown ethers and useful for the same purpose are compounds which differ by the replacement of one or more of the oxygen atoms by other kinds of donor atoms, particularly N or S, such as hexamethyl-[14]-4,11-dieneN$_4$.

Onium salts include quaternary phosphonium salts and quaternary ammonium salts that may be used as the phase transfer catalyst in the process of the present invention. Examples of such compounds include, but are not limited to, tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide, triphenylmethylphosphonium chloride, 4-dialkylaminopyridinium salts such as tetraphenylarsonium chloride, bis[tris(dimethylamino)phosphine]iminium chloride and tetratris[tris(dimethylamino)phosphinimino]phosphonium chloride. One non-limiting example of a phase transfer agent is Aliquat 336.

Polyalkylene glycol compounds useful as phase transfer catalysts include, but are not limited to, glycols such as diethylene glycol, triethylenre glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight about 300) dimethyl ether, polyethylene glycol (average molecular weight about 300) dibutyl ether, and polyethylene glycol (average molecular weight about 400) dimethyl ether.

Cryptates are another class of compounds useful in the present as phase transfer catalysts. These are three-dimensional polymacrocyclic chelating agents that are formed by joining bridgehead structures with chains that contain properly spaced donor atoms. For example, bicyclic molecules that result from joining nitrogen bridgeheads with chains of (—$OCH_2CH_2$—) groups as in 2.2.2-cryptate (4,7,13,16,21,24-hexaoxa-1,10-diasabicyclo-(8.8.8)hexacosane; available under the brand names Crypt and 222 and Kryptofix 222). The donor atoms of the bridges may all be O, N, or S, or the compounds may be mixed donor macrocycles in which the bridge strands contain combinations of such donor atoms.

Phase transfer catalysts may also include those described within U.S. Pat. No. 6,548,719, the contents of which are incorporated herein by reference, and may be provided in an effective amount to effect the desired reaction. Such an amount may include, but is not limited to, a concentration between 0.001 to about 10 mol %.

Dehydrohalogenation may be carried out in a corrosion-resistant reaction vessel and/or a stirred tank reactor. Examples of such materials include, but are not limited to, Hastelloy, Inconel, Monel, and fluoropolymer linings.

The following are examples of the invention and are not to be construed as limiting.

EXAMPLES

Example 1

The liquid phase fluorination of the HCFO-1233xf was conducted in the presence $SbCl_5$. About 6100 grams of $SbCl_5$ were contained in a Teflon™-lined liquid phase reactor (Teflon is a trademark of E.I. duPont de Nemours & Co) equipped with a 2-inch ID (inside diameter) packed column and a condenser. The reactor is 2.75-inch ID×36-inch L (length). A large excess of $Cl_2$ was first added to the reactor to ensure that the catalyst was in a pentavalent state. The reactor was heated to about 85° C.-87° C. HF feed was started first. When 1.3 lbs (pounds) of HF had been added the HCFO-1233xf feed was started. The purity of the HCFO-1233xf feed stock was about 98 GC area % (gas chromatograph). The experiment ran continuously for 71 hours. For this run, chlorine was fed batchwise about every 4 hours throughout the run to keep the catalyst active. The HF and HCFO-1233xf feeds were varied during the run. The feeds averaged 0.495 lbs/hr HF, and 0.408 lbs/hr HCFO-1233xf (chlorine was 5.4% by weight of organic) for a 7.9/1 ratio of HF/HCFO-1233xf, and 135 seconds residence time at the beginning of the run. In the middle of the run, the feeds averaged 0.843 lbs/hr HF (pounds/hour) and 0.66 lbs/hr HCFO-1233xf (chlorine was 3.3% by weight of organic) for a 8.33/1 ratio of HF/HCFO-1233xf, and 80 seconds residence time. For the end of the run, the rate was increased. The feeds for this period averaged 1.42 lbs/hr HF and 1.24 lbs/hr HCFO-1233xf (chlorine was 2% by weight of organic) for a 7.5/1 ratio of HF/HCFO-1233xf, and 47 seconds residence time. The level of unreacted HCFO-1233xf appeared to increase late in the run, which could have been the result of lower $Cl_2$ level or shorter residence time. The reactor temperature range for the experiment was 78-91° C. and the pressure range was 85 psig-115 psig (pounds per square inch gauge). The organic crude material collected from the run was run on a gas chromatograph and had the following GC analysis. The concentrations of HCFC-244bb, HFC-245cb, and HCFO-1233xf in organic phase were 82.9, 11.8 and 1.1 GC Area %, respectively.

Example 2

The dehydrochlorination of HCFC-244bb was carried out in one liter Parr reactor equipped with thermocouple and magnetic stirrer. 15 g Aliquat 336™ was added to reactor. Reactor was then closed and pressure tested. Afterwards 294 g of Organic mixture and 270 g of 45% KOH were added into reactor. The analysis of organic mixture using Gas Chromatography (GC) revealed 8.1 GC Area % of 1234yf, 89.5 GC Area % of 244bb, and 1.8 GC Area % of 1233xf. The stirrer was then turned on and the reactor was heated to 55° C. Upon reaching 55° C. (after about 2 hours), pressure in reactor increased from initial 10 psig to 55 psig. Reactor was held at 55° C. for 4 hours and pressure further increased to 78 psig. A GC analysis of the reactor organic content after the reaction was completed revealed 64.2 GC Area % of 1234yf, 33.2% GC Area of 244bb, 2.2 GC Area % of 1233xf, and 0.4 GC Area % of unknowns.

Example 3

A 10 gallon jacketed metal reactor equipped with an agitator, rectifying column, and condenser (to reflux unreacted organic material back to the reactor) is prepared to run a dehydrofluorination reaction. The reaction being studied is the dehydrofluorination of 1,1,1,2,2-pentafluoropropane (HFC-245cb) to produce 2,3,3,3-tetrafluoropropene (HFO-1234yf). For a first experiment, the reactor is charged with 35.2 lbs of 38 wt % KOH solution and 0.4 lbs of phase transfer catalyst (Aliquat 366). The mixture is then agitated at 420 RPM and heated to 55-60° C. About 27.1 lbs of crude 245cb (94 GC Area % purity) is then added. The reactor pressure rises to about 200 psig and some product is removed from the top of the condenser as it is formed according to the target temperature at the top of the column indicating presence of 2,3,3,3-tetrafluoropropene. The overhead material is dried using a desiccant and collected in a dry-ice trap. A GC analysis of the reactor organic content after the reaction is completed revealing an 80% conversion (molar basis) of 245cb and a 95% selectivity to 1234yf.

Example 4

A 10 gallon jacketed metal reactor equipped with an agitator, rectifying column, and condenser (to reflux unreacted organic material back to the reactor) is prepared to run a dehydrohalogenation reaction. The reaction being studied is the dehydrohalogenation of a mixture of 1,1,1,2-tetrafluoro-2-chloropropane (HCFC-244bb) and 1,1,1,2,2-pentafluoropropane (HFC-245cb) to produce 2,3,3,3-tetrafluoropropene (HFO-1234yf). For a first experiment, the reactor is charged with 35 lbs of 38 wt % KOH solution and 0.4 lbs of phase transfer catalyst (Aliquat 366). The mixture is then agitated at 420 RPM and heated to 55-60 ° C. About 25 lbs of the 244bb/245cb mixture (about 72 GC area % 244bb and 26 GC area % 245cb) is then added. The reactor pressure rises to about 200 psig and some product is removed from the top of the condenser as it is formed according to the target temperature at the top of the column indicating presence of 2,3,3,3-tetrafluoropropene. The overhead material is dried using a desiccant and collected in a dry-ice trap. A GC analysis of the reactor organic content after the reaction is completed reveals a 75% conversion (molar basis) of 244bb, an 80% conversion (molar basis) of 245cb, and an overall 95% selectivity to 1234yf.

We Claim:

1. A process for making 2,3,3,3-tetrafluoropropene, comprising:
    dehydrohalogenating 1,1,1,2-tetrafluoro-2-chloropropane and 1,1,1,2,2-pentafluoropropane in the presence of a caustic agent selected from the group consisting of KOH, NaOH, LiOH, $Mg(OH)_2$, $Ca(OH)_2$, CaO and combinations thereof and within a temperature range from greater than 40° C. to less than or equal to 80° C., wherein the dehydrohalogenating step results in a conversion of at least about 70% of both 1,1,1,2-tetrafluoro-2-chloropropane and 1,1,1,2,2-pentafluoropropane and a selectivity of 2,3,3,3-tetrafluoropropene of at least about 85%.

2. The process of claim 1 wherein the caustic agent is KOH.

3. The process of claim 2 wherein KOH is provided as an aqueous solution comprising from about 5% to about 62% by weight of KOH.

4. The process of claim 1 wherein a reaction pressure of the process ranges from atmospheric pressure, super- atmospheric pressure and sub-atmospheric pressure.

5. The process of claim 1 wherein the dehydrohalogenating step occurs in the presence of a phase transfer catalyst.

6. The process of claim 5 wherein the phase transfer catalyst is selected from the group consisting of crown ethers, onium salts, cryptates, polyalkylene glycols, derivatives thereof, and combinations thereof.

7. A process for preparing 2,3,3,3- tetrafluoropropene, comprising:
    contacting 2-chloro-3,3,3-trifluoropropene with hydrogen fluoride in the presence of a fluorination catalyst to produce an intermediate composition comprising a 1,1,1,2-tetrafluoro-2-chloropropane and a 1,1,1,2,2-pentafluoropropane;
    optionally, recovering the intermediate composition; and
    contacting said intermediate composition with a caustic agent selected from the group consisiting of KOH, NaOH, LiOH, $Mg(OH)_2$, $Ca(OH)_2$, CaO and combinations thereof and at a temperature from greater than 40° C. to less than or equal to 80° C., which results in a conversion of at least about 70% of both 1,1,1,2-tetrafluoro-2-chloropropane and 1,1,1,2,2-pentafluoropropane and a selectivity of 2,3,3,3-tetrafluoropropene of at least about 85%.

8. The process of claim 7 wherein the caustic agent is KOH.

9. The process of claim 8 wherein KOH is provided as an aqueous solution comprising from about 5% to about 62% by weight of KOH.

10. The process of claim 7 wherein a reaction pressure of the process ranges from atmospheric pressure, super- atmospheric pressure and sub-atmospheric.

11. The process of claim 7 wherein the dehydrohalogenating step occurs in the presence of a phase transfer catalyst.

12. The process of claim 11 wherein the phase transfer catalyst is selected from the group consisting of crown ethers, onium salts, cryptates, polyalkylene glycols, derivatives thereof, and combinations thereof.

* * * * *